US00PP09406P

United States Patent [19]

Zaiger et al.

[11] Patent Number: Plant 9,406

[45] Date of Patent: Dec. 19, 1995

[54] NECTARINE TREE 'ARCTIC GOLD'

[76] Inventors: Chris F. Zaiger, 929 Grimes Ave.; Gary N. Zaiger, 1907 Elm Ave.; Leigh M. Gardner, 1207 Grimes Ave.; Grant G. Zaiger, 4005 California Ave., all of Modesto, Calif. 95358

[21] Appl. No.: 386,988

[22] Filed: Jan. 24, 1995

[51] Int. Cl.[6] ..... A01H 5/00

[52] U.S. Cl. ..... Plt./40.1

[58] Field of Search ..... Plt./40.1

*Primary Examiner*—James R. Feyrer

[57] ABSTRACT

A new and distinct variety of nectarine tree which has the following unique combination of desirable features that are outstanding in a new variety:

1. Fruit with excellent flavor and eating quality.
2. Heavy and regular production of white flesh freestone fruit.
3. Fruit with firm white flesh having good handling and shipping quality.
4. Vigorous, upright growth habit.
5. Fruit with a high degree of red skin color.
6. Relatively uniform large fruit throughout the tree.
7. Ability of the fruit to hold firm on the tree 7–10 days after maturity (shipping ripe).

1 Drawing Sheet

ORIGIN OF THE VARIETY

The present new variety of nectarine tree was originated by us in our experimental orchard located near Modesto, Calif., as a fifth generation seedling from a cross between Ruby Gold Nectarine (U.S. Plant Pat. No. 3,101) and Redwing Peach (U.S. Plant Pat. No. 621). A large group of these fifth generation seedlings were planted and maintained under careful observation by us, during which time, one such seedling, which is the present variety, having especially desirable fruit characteristics was selected for asexual reproduction and commercialization.

ASEXUAL REPRODUCTION OF THE VARIETY

The present new and distinct variety of nectarine tree was asexually propagated by budding, as performed by us in our experimental orchard located near Modesto, Calif., and the asexually propagated trees show that all said characteristics of the tree and its fruit are established and transmitted through succeeding propagations.

SUMMARY OF THE VARIETY

The present new variety of nectarine tree is of large size, vigorous upright growth and is a prodcutive and regular bearer of large, firm, white flesh, freestone fruit with excellent flavor and eating quality. The fruit is further characterized by being relatively large in size throughout the tree, having good handling and shipping quality, having a high degree of attractive red skin color and in comparison to its maternal parent Ruby Gold Nectarine (U.S. Plant Pat. No. 3,101), the new variety is white flesh instead of yellow and is approximiately 35 days later in maturity.

DESCRIPTION OF THE PHOTOGRAPHS

The accompanying photographic reproduction in color show typical specimens of the fruit and foliage of our new nectarine variety. The illustrations show the upper and lower surface of the leaves, and an exterior and sectional view of the fruit, with the fruit divided on the suture plane to reveal flesh coloration, pit cavity and a stone remaining in place. The photographs were taken shortly after the fruit was picked at maturity (firm ripe) and the colors are as nearly true as is reasonably possible in a color representation of this type.

DESCRIPTION OF THE VARIETY

The following is a detailed botanical description of the new and distinct variety of nectarine tree, its flowers, foliage and fruit, as based on observations of the specimen grown in our experimental orchard located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearing.*—Regular.
- *Productivity.*—Productive.

Trunk:
- *Size.*—Medium.
- *Texture.*—Medium shaggy.
- *Color.*—Brown to grayish brown (5-E-4) to (5-E-6).

Branches:
- *Size.*—Medium.
- *Surface.*—Smooth to medium rough. Varies with age of growth.
- *Lenticels.*—Numerous. Medium size.
- *Color.*—Light brown to brown — varies with maturity.

Leaves:
- *Size.*—Large. Average length 7½". Average width 1¾".
- *Texture.*—Smooth.
- *Form.*—Lanceolate. Pointed.
- *Margin.*—Crenate.
- *Thickness.*—Medium.
- *Glands.*—Reniform. Number varies from 2 to 6. Average number 3. Positioned on base of the leaf blade and upper portion of petiole.
- *Petiole.*—Medium length. Medium thickness.
- *Color.*—Upper surface — green to dark green (29-F-5) to (29-F-8). Lower surface — grayish green to green (29-E-4) to (29-E-6).

Flower buds:
- *Size.*—Medium to large.
- *Length.*—Medium.
- *Form.*—Plump.

Flowers:
- *Size.*—Large — showy.
- *Blooming period.*—Mar. 5, 1994 to Mar. 12, 1994. Varies slightly with climatic conditions.

*Pollen.*—Present — self fertile.
*Color.*—Pink.

Fruit:
*Maturity when described.*—Firm ripe.
*Date of first picking.*—Jul. 15, 1994.
*Date of last picking.*—Jul. 21, 1994.
*Size.*—Large — comparatively uniform. Average diameter axially 2⅞" to 3¼". Average transversely in suture plane 2⅝" to 3".
*Form.*—Nearly globose, slightly larger on one side. Slightly flattened at stem. Slight apical tip.
*Suture.*—Shallow — extends from base to apex.
*Ventral surface.*—Rounded, very slightly lipped.
*Cavity.*—Rounded to slightly elongated in suture plane. Average depth — ½". Average breadth — 1".
*Base.*—Retuse.
*Apex.*—Varies from rounded to slight pistil point.

Flesh:
*Ripens.*—Evenly.
*Texture.*—Firm.
*Juice.*—Moderate.
*Eating quality.*—Excellent.
*Flavor.*—Excellent.
*Amygdalin.*—Undetected.
*Aroma.*—Slight.
*Fibers.*—Few, small, tender.
*Color.*—White 2-A-1. Pit cavity — red to turkish red (10-B-8) to (10-D-8). Bleeding to red into flesh from pit cavity.

Skin:
*Thickness.*—medium.
*Texture.*—Tough, tenacious to flesh.
*Tendency to crack.*—None.
*Down.*—Wanting.
*Color.*—Ground color, white to pinkish white (10-A-1) to (10-E-8). Overspread with red to dark red (10-C-8) to (10-E-8).

Stone:
*Type.*—Freestone.
*Size.*—Large. Average length 1½". Average breadth 1⅛". Average thickness ¾".
*Form.*—Ovoid.
*Base.*—Straight.
*Apex.*—Acuminate.
*Sides.*—Varies from equal to unequal.
*Surface.*—Irregularly furrowed toward apex, pitted toward base. Pit cavities vary from round to elongated.
*Ridges.*—Rounded.
*Tendency to split.*—None.
*Color.*—Brown to cinnamon brown (6-D-7) to (6-E-7).

Use: Dessert.
*Market.*—Local and long distance.

Keeping quality: Good.

Shipping quality: Good.

The present new variety of nectarine tree, its flowers, foliage and fruit herein described, may vary in slight detail due to variations in soil types, cultural practices and climatic conditions under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth and by being a productive and regular bearer of large, firm white flesh, freestone fruit with excellent flavor and eating quality; the fruit is further characterized by having a high degree of attractive red skin color, having the ability to stay firm on the tree 7 to 10 days after maturity, having good handling and shipping quality and in comparison to its maternal parent Ruby Gold Nectarine (U.S. Plant Pat. No. 3,101) the new variety is approximately 35 days later in maturity.

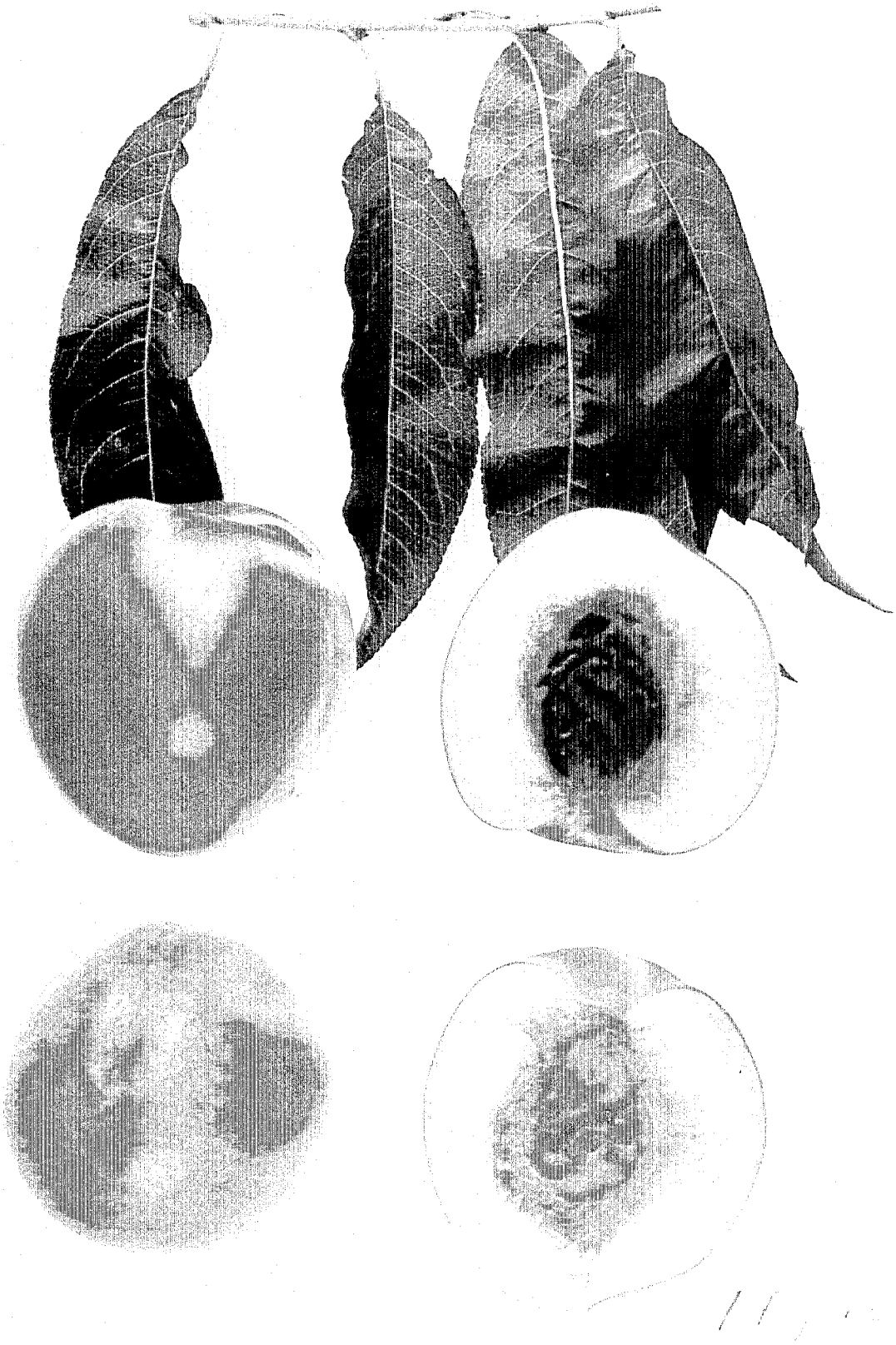

* * * * *